United States Patent [19]
Märin

[11] Patent Number: 5,849,740
[45] Date of Patent: Dec. 15, 1998

[54] METHODS FOR USING KETOCONAZOLE AND RELATED SUBSTANCES IN MEDICAMENTS FOR TREATMENT OF TYPE II DIABETES

[75] Inventor: Per Märin, Göteborg, Sweden

[73] Assignee: Cortendo AB, Gothenburg, Sweden

[21] Appl. No.: 776,983

[22] PCT Filed: Aug. 9, 1994

[86] PCT No.: PCT/SE94/00729

§ 371 Date: Feb. 6, 1997

§ 102(e) Date: Feb. 6, 1997

[87] PCT Pub. No.: WO96/04912

PCT Pub. Date: Feb. 22, 1996

[51] Int. Cl.⁶ .......................... A61K 31/50; A61K 31/56; A61K 31/415; A61K 31/335
[52] U.S. Cl. .......................... 514/247; 514/178; 514/396; 514/467; 514/866

[58] Field of Search ...................... 514/247, 396, 514/467, 866, 178

[56] References Cited

U.S. PATENT DOCUMENTS

| | | | |
|---|---|---|---|
| 5,175,144 | 12/1992 | Walser | 514/2 |
| 5,432,176 | 7/1995 | Walser | 514/252 |
| 5,591,736 | 1/1997 | Walser | 514/178 |

*Primary Examiner*—Kevin E. Weddington
*Attorney, Agent, or Firm*—Hopgood, Calimafde, Kalil & Judlowe, LLP

[57] ABSTRACT

The present invention is a method of using ketoconazole or molecules resembling ketoconazole with comparable biological activity for the manufacture of drugs and for medical treatment of diabetes mellitus type II as well as for counteracting the other risk factors associated with the Metabolic Syndrome.

7 Claims, No Drawings

METHODS FOR USING KETOCONAZOLE AND RELATED SUBSTANCES IN MEDICAMENTS FOR TREATMENT OF TYPE II DIABETES

The present invention relates to the use of ketoconazole or molecules resembling ketoconazole but with some side-chains, not affecting the biological activity compared to ketoconazole, changed for manufacturing drugs for treatment of diabetes mellitus type II.

The drug ketoconazole (Trade name Fungoral™) is a well- documented drug for treatment of fungal infections. The process of making ketoconazole is well known and described. In this invention Fungora™ capsules aimed at oral administration should be used. This means that Fungoral™ should be administered the same way (oral) and in the same composition that is already well-known on the market for treatment of fungal infections the oral route. Therefor it is not considered necessary to further describe the process of making Fungoral™. For the same reason it is not considered necessary to give a full, clear, concise and exact term of this drug, since it is already well known for persons skilled in the art of medicine.

The drug comprising ketoconazole (Trade name Fungoral™) and chemically closely related substances, the mode of operation of which is to influence the normal cortisol synthesis in the adrenal glands in such a way that the production of biologically perfectly acting cortisol is partly inhibited, is intended to be used for medical treatment of diabetes mellitus type II in men and women as well as for counter-acting the risk factors which are parts of the Metabolic Syndrome (also known as "the deadly quartet" or "Syndrome X" or the "Insulin Resistance Syndrome"), which is characterised by an accumulation of risk factors for cardiovascular disease, stroke and diabetes mellitus type II, i.e. insulin resistance, hyperinsulinemia, abdominal obesity, (caused by an accumulation of intra-abdominal fat), elevated serum lipids, and raised blood pressure, as well as reducing the risk of development of these diseases.

In this new invention ketoconazole shall be administered the oral route in doses of 100–800 mg daily. The drug can be administered once or several times daily. At present a dose of 400 mg administered in the evening has been proven to be the best mode. However, we also claim that administration at other points of time, and in other doses (100–800 mg) can be equally effective.

Since ketoconazole is also inhibiting the normal production of testosterone in men, it is possible that this sex needs a certain amount of testosterone supplementation when treated with ketoconazole, to have an optimal effect of the treatment.

We have investigated a group of people with diabetes mellitus type II. They have been treated with ketoconazole during 2 and 6 weeks, respectively. Investigations before and after treatment have shown a decrease in blood glucose measured either in the fasting state or at 2 hours after an intravenous glucose infusion, and most important, a remarkable improvement of insulin sensitivity. More exact data from these studies are given in the tests described below.

Since a decreased insulin sensitivity is a central part of "The metabolic syndrome", also known as "The deadly quartet", "Syndrome X" or the "Insulin Resistance Syndrome" we also claim that fungoral treatment to people with risk factors according to this syndrome should be expected to be effective also for treatment of these specific risk factors (abdominal obesity, hypertension, elevated blood lipids) as well as for decreasing the risk for diseases caused by these risk factors (Cardiovascular disease such as coronary artery disease, other arteriosclerotic manifestations including stroke).

The mechanism of the action of ketoconazole is that the substance influence the cortisol synthesis of the adrenal glands in such a way that a sub-fraction of a biologically non-perfect substance similar to cortisol, so called "crippled cortisol", is formed instead of the normal cortisol molecule.

The cortisol antagonistic effect of the drug is considered to have a central importance for the positive effects on the risk factors mentioned above, decreasing the metabolic activity of fat inside the abdominal cavity, which in turn leads to a decreased fat infiltration of the liver, improving the glucose homeostasis over the liver and peripherally in the tissues in turn leading to improvement of diabetes mellitus type II (decreasing blood glucose and increasing insulin sensitivity), reducing the serum lipids through improvement of the regulating mechanisms in the liver and also inhibiting cholesterol synthesis by a direct effect on the adrenal glands. A positive effect on the blood pressure can also be expected via the cortisol-antagonistic effect.

The scientific basis for these effects can be explained by an inhibition of the physiologically increased cortisol secretion rate that is known to be present under the conditions described above. (The metabolic syndrome and its synonyms described above). This increased cortisol secretion can per se explain all the parts of the syndrome described including the development of diabetes mellitus type II. The scientific explanation for the beneficial effects of ketoconazole on the treatment of diabetes mellitus type II is its effects of decreasing the secretion of biologically active cortisol.

The basic substance is ketoconazole in the chemical form which is known and well documented in the literature. This substance can be further chemically modified while maintaining the same biological effects by exchange of different molecular side chains. These substances similar to ketoconazole can then be expected to have similar and/or better effects on the cortisol inhibiting mechanism, which is described above.

A positive effect on the treatment of patients with diabetes mellitus type II with ketoconazole has been shown in that after the administration of ketoconazole a reduction of the insulin insensitivity (resistance), which is often associated with this disease, has been measured. This has been measured as an improved (i.e. reduced) insulin resistance measured with a so called euglychemic glucose clamp method. Thus, the examined patients have improved with regard to their diabetes, measured in the above described way, which in parallell also have resulted in lower blood glucose after treatment compared to before treatment.

The category of patients, that would have an especially good use of ketoconazole are patients with diabetes mellitus type II with insulin insensitivity and despite treatment with usual anti-diabetic drugs and/or insulin still have remaining elevated glucose values in the blood in fasting condition as well as after a meal. The investigated patients had decreased insulin sensitivity compared to healthy persons, measured by euglychemic glucose clamp. Supply of ketoconazole to this category of patients has been shown to have a positive and specific effect on the insulin insensitivity in such a way that their diabetes mellitus type II was improved. This was measured as improved insulin sensitivity and lower blood glucose.

Other positive effects have also been detected among these patients: Reduced cholesterol levels in the plasma as well as decreasing blood pressure values.

Results of Clinical tests of women with diabetes mellitus type II, treated with ketoconazole.

Group 1 consists of 3 patients (mean age: 46 years) treated with ketoconazole for 2 weeks, administered orally 22.00 in the evening in the dose of 400 mg.

Group 2 consists of 5 patients (mean age: 51 years) treated with ketoconazole for 6 weeks, administered orally 22.00 in the evening in the dose of 400 mg. Results are expressed as mean values within groups.

| Variables studied | Group 1 | | Group 2 | |
|---|---|---|---|---|
| | Before t. | After t. | Before t. | After t. |
| Fasting blood glucose (mmol/L) | 10.20 | 8.77 | 7.20 | 7.10 |
| Blood glucose (mmol/L) 2 hours after start of an i.v. glucose infusion | 9.73 | 7.90 | 6.48 | 5.76 |
| GIR (glucose infusion rate during euglycemic glucose clamp expressed as mg glucose per minute divided by lean body mass), indicating insulin sensitivity | 0.9 | 1.85 | 2.97 | 4.32 |
| Fasting serum total cholesterol (mmol/L) | 5.80 | 5.67 | 4.80 | 4.10 |
| Systolic blood pressure (mm Hg) measured after 5 min. in supine position. 2 measurements averaged | 140 | 135 | 125 | 123 |
| Diastolic blood pressure (mm Hg) measured after 5 min. in supine position. 2 measurements averaged | 70 | 70 | 75 | 72 |
| Serum-ASAT ($\mu$kat/L) | 0.36 | 0.33 | 0.26 | 0.25 |
| Serum-ALAT ($\mu$kat/L) | 0.61 | 0.52 | 0.40 | 0.37 |

I claim:

1. A method for treating type II diabetes mellitus and counteracting the symptoms presented by the Metabolic Syndrome, with a therapeutic amount of ketoconazole or a derivative thereof having a corresponding activity as an inhibitor of cortisol synthesis.

2. The method of claim 1, wherein said Metabolic Syndrome is selected from the group consisting of The Deadly Quartet, Syndrome X and the Insulin Resistance Syndrome.

3. A method for treating type II diabetes mellitus and counteracting the symptoms presented by the Metabolic Syndrome, comprising the administration of a therapeutic amount of an inhibitor of cortisol synthesis and the co-administration of a therapeutic amount of testosterone.

4. The method of claim 3, wherein said inhibitor of cortisol synthesis is ketoconazole.

5. The method of claim 3, wherein the daily dose rate for said inhibitor is between 100 and 800 mg.

6. A method for treating type II diabetes mellitus and counteracting the symptoms presented by the Metabolic Syndrome, comprising the administration of a therapeutic amount of ketoconazole and the synergistic administration of a therapeutic amount of testosterone.

7. The method of claim 6, wherein the daily therapeutic amount of said ketoconazole is between 100 and 800 mg.

* * * * *